US009301898B2

(12) United States Patent
Cehic

(10) Patent No.: US 9,301,898 B2
(45) Date of Patent: Apr. 5, 2016

(54) DEVICE FOR PASSIVE MOVEMENT OF THE FINGERS

(76) Inventor: Aldo Cehic, Bosco Chiesanuova (IT)

(*) Notice: Subject to any disclaimer, the term of this patent is extended or adjusted under 35 U.S.C. 154(b) by 654 days.

(21) Appl. No.: 13/805,258

(22) PCT Filed: Jul. 1, 2011

(86) PCT No.: PCT/IB2011/052927
§ 371 (c)(1),
(2), (4) Date: Jan. 14, 2013

(87) PCT Pub. No.: WO2012/004716
PCT Pub. Date: Jan. 12, 2012

(65) Prior Publication Data
US 2013/0144195 A1 Jun. 6, 2013

(30) Foreign Application Priority Data
Jul. 6, 2010 (IT) ................................ VI2010A0188

(51) Int. Cl.
*A61M 11/00* (2006.01)
*A61H 1/00* (2006.01)
*A61H 1/02* (2006.01)
*A61H 23/00* (2006.01)

(52) U.S. Cl.
CPC ................ *A61H 1/00* (2013.01); *A61H 1/0288* (2013.01); *A61H 23/00* (2013.01); *A61H 2201/1215* (2013.01); *A61H 2201/1238* (2013.01); *A61H 2201/1659* (2013.01); *A61H 2201/1666* (2013.01); *A61H 2201/1671* (2013.01); *A61H 2201/5007* (2013.01)

(58) Field of Classification Search
CPC ............... A63B 23/16; A63B 21/1438; A63B 21/1442; A63B 21/1469; A61H 1/0285; A61H 1/0288; A61H 2205/065; A61H 2205/067; A61H 15/0092; A61H 1/00; A61H 1/02; A61H 2001/0203; A61H 2201/0157; A61H 2201/1664; A61H 2201/1666; A61H 2201/1215; A61H 2201/1238; A61H 2201/1659; A61H 2201/1671; A61H 2201/5007
USPC ......... 623/57, 64; 482/44, 47, 48; 601/40, 33, 601/5, 41, 23, 84
See application file for complete search history.

(56) References Cited

U.S. PATENT DOCUMENTS

| | | | | | |
|---|---|---|---|---|---|
| 1,204,437 | A * | 11/1916 | Heinze | ........................... | 482/48 |
| 1,707,151 | A * | 3/1929 | Thomas | ........................... | 482/47 |
| 4,875,469 | A * | 10/1989 | Brook et al. | ..................... | 601/40 |
| 4,945,902 | A * | 8/1990 | Dorer et al. | ..................... | 602/38 |
| 5,327,882 | A | 7/1994 | Saringer | | |
| 5,451,191 | A * | 9/1995 | Beenken | ........................ | 482/47 |
| 6,443,874 | B1 * | 9/2002 | Bennett | ........................... | 482/44 |
| 7,862,522 | B1 * | 1/2011 | Barclay et al. | ................ | 600/595 |
| 8,574,178 | B2 * | 11/2013 | Tong et al. | ...................... | 601/40 |
| 2010/0305717 | A1 * | 12/2010 | Tong et al. | ...................... | 623/64 |

FOREIGN PATENT DOCUMENTS

| | | |
|---|---|---|
| DE | 3917938 | 12/1990 |

* cited by examiner

*Primary Examiner* — Steven Douglas
(74) *Attorney, Agent, or Firm* — Themis Law

(57) ABSTRACT

A device for the passive movement of the fingers for the therapeutic treatment of a patient includes a plurality of supporting elements, each one adapted to receive a finger of a patient, and a movement unit having a plurality of actuating elements each one operatively connected to one respective of the supporting elements so as to move it with movements uncoordinated from the movements of the other supporting elements which are moved with other actuating elements; a plurality of motion transmission members each one interposed between one of the actuating elements and one respective of the supporting elements and all of them designed to move the supporting elements with three degrees of freedom.

10 Claims, 1 Drawing Sheet

DEVICE FOR PASSIVE MOVEMENT OF THE FINGERS

FIELD OF THE INVENTION

The present invention generally finds application in the technical field of devices for the therapeutic treatment of the human body and particularly relates to a device for the passive movement of the fingers of a patient.

BACKGROUND OF THE INVENTION

Among the devices for the therapeutic treatment of the human body some are studied to stimulate the mobility of the fingers of a hand or of a foot. These devices are particularly useful for the recovery of this mobility in patients who had surgical interventions or traumas for which a period of immobilisation of the limb has been necessary.

The same devices are also used to make a massage of the fingers. Therefore the massage is not made only to improve their mobility, but also as a relaxing therapy of the person. It is in fact known that the mobility of the fingers, as well as of other parts of the body, is strictly connected to the brain, so that a stimulation like the passive movement of the fingers, if appropriately made, may lead to a relaxation of the mind.

Typically, the prior art devices have a shape suitable to receive the end part of the fingers to be moved. Moreover, they are provided with a plurality of duly moved catching elements of the fingers, often constituted by real thimbles.

The type of movement, of course, represents a basic aspect of the prior art devices. Some of them, for example, have mechanisms that generate a repeated movement of traction and extension of the fingers. This movement typically takes place simultaneously for all the fingers of the hand.

Other devices generate a lateral translating movement of the fingers which takes place on the plane defined by the palm of the hand. In other cases to this movement is also associated a movement of traction and extension which, added to the former, allows the movement of the fingers with two degrees of freedom.

In any case, all movements are typically generated by a single motorization organ, and by a mechanic transmission of motion that generates coordinated and repeated movements of the fingers of the hand. This, in fact, allows to have muscles and tendons constantly work.

However, the above devices have some known drawbacks.

First of all, as mentioned, they generally induce movements with only one or two degrees of freedom. This means that the muscles and tendons of the fingers are stimulated only in some directions in the space and not in all directions, so losing the possibility of a rapid rehabilitation or of a complete massage.

Moreover, as mentioned, the movements are coordinated and not randomized.

It has previously been said that the massage of the fingers of the hands as well as of the feet, may induce a state of relaxation of the mind. This is due to the fact that the mind is generally strained to control the movements of all the parts of the body. If a randomized and irregular movement is induced to one of these parts, the mind loses the control thereof. In this case, therefore, the mind is relieved of a part of the work of controlling the body, so as to free it from this occupation. It is to be considered that it has been estimated that at the cortical level the control of the movement of the fingers and of the hand takes about the 35% of the sensory-motor area of the whole body. In the case of the fingers of the hand, a repeated and coordinated movement does not allow to induce the mind to lose its control on them.

This drawback influences also therapies for the motory rehabilitation of the fingers following atrophy, surgical operations or traumas. In fact, if the mind continues to try to control the movement of the fingers, it induces a muscular opposition to the said movements. This leads to a state of tension of the muscles and of the tendons which counteracts the motory rehabilitation. In fact it is known that any form of muscular rehabilitation is accelerated if the passive movement of the muscle is made when the muscle is relaxed.

SUMMARY OF THE INVENTION

A main object of this invention is to overcome, at least in part, the above drawbacks, by providing a device for the passive movement of the fingers for the therapeutic treatment of a patient which allows to move each finger with uncoordinated movements as for the other fingers.

Another object of the present invention is to provide a device for the passive movement of the fingers which induces movements with three degrees of freedom.

These and other object, as better explained hereafter, are fulfilled by a device for the passive movement of the fingers for the therapeutic treatment of a patient according to one or more of the following claims which are integrant part of the present description.

In particular, the device may comprise a plurality of supporting elements each one susceptible to receive at least one finger of the patient. They may consist, for example, of a hollow body susceptible to house and hold at least one distal portion of the finger. In other words, each of them may consist of a thimble.

According to another aspect of the invention, the device for the passive movement of the fingers may also comprise at least one movement unit provided with actuating means for the generation of the movement. Each actuating mean may be operatively connected to at least one respective supporting element so as to move it with movements which are uncoordinated from the movements of one or more of the other supporting elements which, on turn, are moved by different actuating means.

According to another aspect of the invention, the movement unit comprises a plurality of motion transmission means, each one interposed between at least one actuating mean and one respective supporting element, and all designed to move the supporting elements with three degrees of freedom.

In other words, the device may comprise a plurality of mechanisms, with electric, hydraulic or mechanic actuation, which set into motion the patient's fingers in a substantially unconnected way with each other. In this way the mind loses the control of the fingers and the massage is not hampered. Moreover, also the result of relaxing the mind is achieved, having relieved it of this occupation.

It is also observed that the device of the invention may move the fingers according to three degrees of freedom, so allowing a movement as complete as possible. This can be achieved, for example, by providing each one of the motion transmission means by at least one first transmission element susceptible to move the respective supporting element with at least two degrees of freedom. For the third degree of freedom each of the motion transmission means may comprise at least one second transmission element susceptible to move the respective supporting element according to one or more degrees of freedom among which it must be present the third degree of freedom.

BRIEF DESCRIPTION OF THE DRAWINGS

Further features and advantages of the invention will appear more evident upon reading the detailed description of a preferred, non-exclusive embodiment of a device for the passive movement of the fingers for the therapeutic treatment of a patient according to the invention, which is described as non limiting example with the help of the annexed drawings, in which.

DETAILED DESCRIPTION OF SOME PREFERRED EMBODIMENTS

Figure 1:
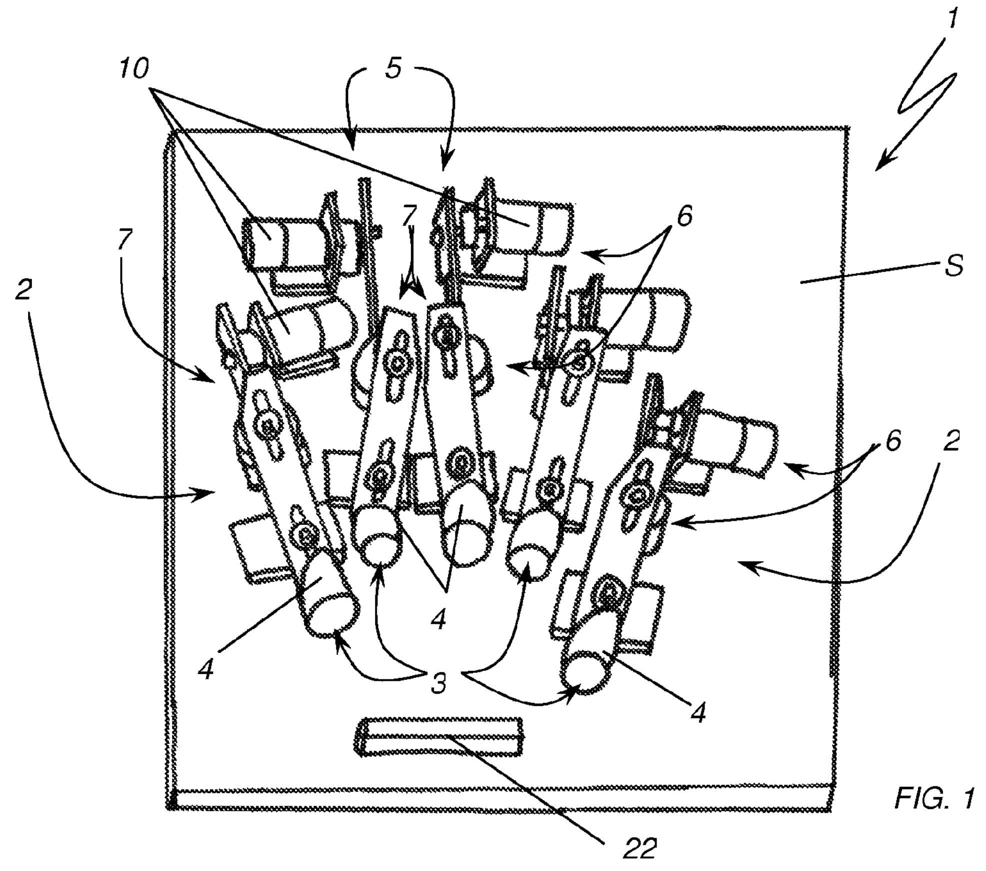
FIG. 1 represents a device according to the invention in a schematic axonometric view.

Referring to the above figures, and particularly to FIG. 1, a device 1 for the passive movement of the fingers for the therapeutic treatment of a patient is described. The above figures refer to a device 1 for the movement of the fingers of the hand; however it is evident that this shall not be meant in a limiting way for different forms of implementation aimed to the therapeutic treatment of the feet.

Evidently, the device 1 comprises a plurality of supporting elements 2 each susceptible to receive at least one finger of the patient.

Typically, but not necessarily, the supporting elements 2 comprise a hollow body 3 susceptible to house and hold at least one distal portion of the finger. In other words, the supporting elements 2 typically comprise thimbles 4. However, the scope of the invention includes also different embodiments of the invention, according to which, for example, the supporting elements may consist of rings where the distal part of the finger may be inserted, possibly combined with shaped elements where said distal portion may be laid.

According to an aspect of the invention, the device 1 comprises a movement unit 5 of the supporting elements 2. This movement unit 5 on turn comprises actuating means 6, to generate the motion, and a plurality of motion transmission means 7, each one interposed between the actuating means 6 and one respective supporting element 2 to move it according to three degrees of freedom.

Advantageously, therefore, the device 1 is provided with a movement unit 5 designed to subject a patient's fingers to movements with three degrees of freedom, that is in the tridimensional space. This allows, differently from the above described prior art where the movements are always in a bidimensional space, to stimulate tendons and muscles in every direction with movements suitable to ensure a complete massage or a quick therapeutic recovery.

As far as the actuating means 6 are concerned, each of them is operatively connected to one respective supporting element 2, so as to move it with movements which are uncoordinated or unconnected from the movements to which are subjected the other supporting elements, whereof each one is moved by means of a different respective actuating mean.

In this way, therefore, each patient's finger is moved with movements which may be totally independent from the movements to which the other fingers are subjected.

Consequently, advantageously, the mind loses their control reaching a state of mental and physical relaxation concerning muscles and tendons. In fact, as mentioned, the mind can't tend them to oppose to uncontrolled movements. In this way there is a de-synchronization at the cortical level.

The described and represented embodiment shall however not be considered as limiting for other different embodiments. In particular, the basic aspect is that there are more actuating means for moving in an uncoordinated way, that is in an unconnected and independent way, one or more fingers in respect to the other ones. The minimum case refers to two different actuating means which move two different fingers groups of the same hand or foot. However the optimal case occurs when there are different actuating means for each finger.

As far as the embodiment of the actuating means 6 is concerned, it is evident that they may be of various types, that is of electric, mechanical, hydraulic type. In the case represented in the figures they are constituted by motors 10 associated to the motion transmission means 7, however this hasn't to be meant in a limiting sense.

Figure 2:
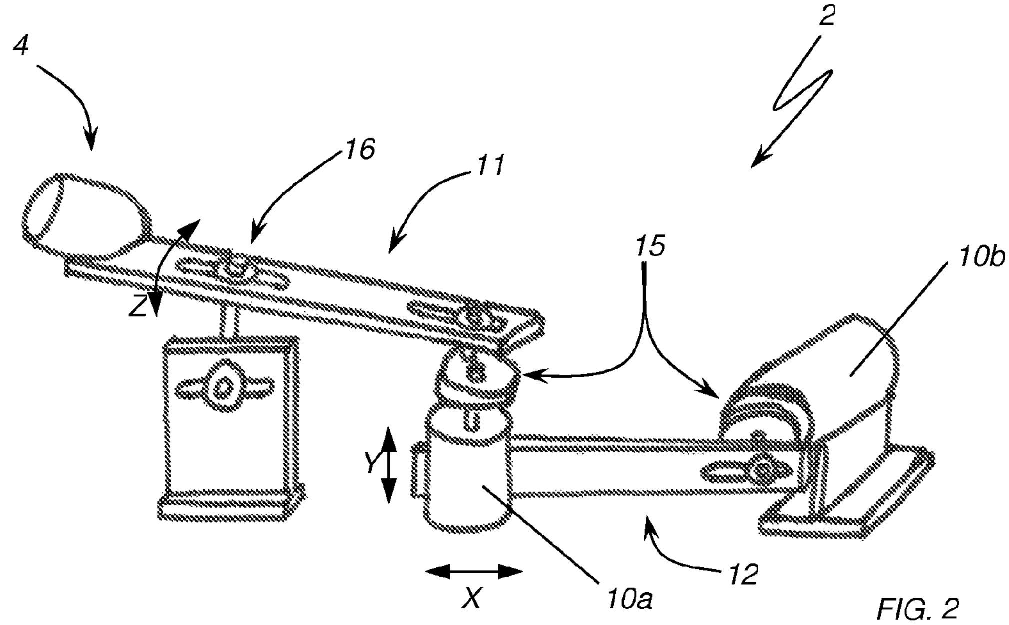
FIG. 2 represents a detail of FIG. 1.

It is equally evident that the represented embodiment hasn't to be meant as limiting in the number of used motors 10 either. In the example case, in fact, each of the motion transmission means 7, as can be seen in FIG. 2, comprises two transmission elements 11, 12. A first 12 thereof is susceptible to move the respective supporting element 2 along two directions X, Y substantially orthogonal to each other, whereas the second transmission element 11 is susceptible to move the supporting element 2 along a third direction Z incident to the plane defined by the directions X and Y. In particular, the transmission elements 11 and 12 are moved by the motors 10*a*, 10*b* with a system of "crank-shaft" type using eccentric rotating means 15, for example constituted by eccentric rotary joints, but also this case is only a non limiting embodiment. For example it is possible to use, as an alternative, non eccentric rotary joints, pairs of plungers susceptible to generate a movement with two degrees of freedom or other.

In the described embodiment, the joint 16 is such as to allow to develop movements along the three axis X, Y and Z incident to each other so to have the thimble 4 develop a complete movement in the tridimensional space. In particular, the motor 10*a*, unitary with the support S, moves the transmission element 12, and with it the motor 10*b* and the transmission element 11, along two directions X and Y. The motor 10*b*, then, also with the "crank-shaft" system, adds the movement on the axis Z.

According to another aspect of the invention, the actuating means 6 which move the two transmission elements 11, 12 comprise a pair of motors 10*a*, 10*b*. However, it is also possible that in different embodiments there are more actuating means for the movement of each finger. For example, an alternative embodiment may have the use of a different motor for the generation of movement along each of the three directions.

In other words, alternative embodiments are possible, for which the number of motors may be different committing the performance of a motion with three degrees of freedom to the motion transmission means. The use of two motors for each supporting element or of three motors, one for each degree of freedom, or a single motor may be provided. In this last case the motion transmission means have to be more complex.

Other embodiments may distinguish themselves by the number of motion transmission elements interposed between the actuating means and each supporting element. For example, in some cases a single transmission element may be provided which generates the movement according to all three degrees of freedom. In other cases it is instead possible to have the use of at least three transmission elements, each one committed to the movement with a single degree of freedom. To each one of the said transmission elements may be connected a committed motor or all may be connected to a single motor, or, furthermore, they may be divided into functional groups whereof each one is connected to a respective motor.

Moreover, as the actuating means may be of different types, also the transmission means may be manufactured in different ways. In the case of hydraulic actuators, for example, the transmission means may consist of plungers working with fluid which generate the movement according to a single degree of freedom. In this case, therefore, for each supporting element at least three motion transmission elements are necessary.

According to further embodiments, the device may comprise vibrations generating means associated to the supporting elements to induce them a vibratory movement. As known, this movement helps to induce a state of muscular relaxation.

According to another aspect of the invention, the device 1 also comprises a logical control unit which is not represented in the figures. It is connected to the actuating means 6 to control the motion of the supporting elements 2. In this way it is possible to adjust the trajectory and the speed of the movements to the patient and to the therapy to apply. Furthermore, the control of the actuating means by means of the logical control unit allows to improve the lack of relation between the movements generated by each of the different actuating means 6. It is evident that the greater the number of motors 10 used and connected to the logical control unit, the greater the degree of unconnection achievable in the movement of the supporting elements 2 is.

According to a possible alternative embodiment, which is not represented in the figures, the logical control unit is also associated to the motion transmission means. In this case these last ones have transmission elements adjustable by the logical control unit so that the movement, while performed, allows such further variations as to lead to a higher degree of uncoordination among the passive movement to which the fingers are subjected.

According to another aspect of the invention, the device 1 is also provided with adjusting means to adjust the different parts to the specific anatomic sizes of the patient. In particular, even if not represented, there are adjusting means to adjust the length and the angle of reciprocal disposition of the motion transmission means 7 so that the device 1 is equally usable with hands of different sizes to each other. It is evident that these adjusting means may be connected to the logical control unit to simplify the control thereof by an operator.

According to another aspect of the invention, the device 1 comprises a supporting portion 22 of a hand which may also be provided with a holding element of the hand on the supporting portion 22 during the therapeutic treatment. In other words, in order to improve the therapeutic treatment the hand is laid on the supporting portion 22 to simplify the relaxation thereof. The stability of such position may be committed to a restraint element. Totally equivalent is the case of a device for the therapeutic treatment of the feet.

The above disclosure clearly shows that the device for the passive movement of the fingers for the therapeutic treatment of a patient according to the invention fulfils the intended objects and, in particular, overcomes the drawbacks of the prior art allowing to move the fingers with non repeated movements substantially different for each finger.

Furthermore, the induced movements have three degrees of freedom.

The device for the passive movement of the fingers for the therapeutic treatment of a patient according to the invention is susceptible to many changes and variants, all falling within the inventive concept expressed in the annexed claims. All particulars may be replaced by other technically equivalent elements, and the materials may be different according to the needs, without departing from the field of the invention.

Even if the device for the passive movement of the fingers of a patient have been described with particular reference to the accompanying figures, the numerals referred to in the disclosure and claims are only used for the sake of a better intelligibility of the invention and shall not be intended to limit the claimed scope in any manner.

The invention claimed is:

1. A device for passive movement of fingers for medical treatment of a patient comprising:

a plurality of supporting elements, each one adapted to receive at least one finger of a patient; and at least one movement unit comprising:

a plurality of actuating means each one operatively connected to at least one of said supporting elements to move said at least one of said supporting elements with movements uncoordinated to movements of at least one other of said supporting elements, which is moved by another one of said actuating means; and a plurality of motion transmission means, each interposed between at least one of said actuating means and to a respective supporting element and designed to move said supporting element with at least three degrees of freedom.

2. The device according to claim 1, wherein each of said motion transmission means comprises at least a first transmission element adapted to move said respective supporting element with at least two degrees of freedom.

3. The device according to claim 1, wherein each of said motion transmission means comprises at least a second transmission element adapted to move said respective supporting element with at least one degree of freedom.

4. The device according to claim 1, wherein each of said motion transmission means comprises at least two transmission elements, at least one of said at least two transmission elements being adapted to move said respective supporting element in at least two incident directions.

5. The device according to claim 1, wherein said motion transmission means comprise eccentric rotation means.

6. The device according to claim 1, wherein each of said supporting elements comprises a hollow body adapted to house and hold at least one distal portion of a finger.

7. The device according to claim 1, further comprising at least one logical control unit operatively connected to at least said actuating means to control the movements of each of said supporting elements.

8. The device according to claim 7, wherein said logical control unit is operatively connected also with each of said motion transmission means.

9. The device according to claim 1, further comprising at least a supporting portion adapted to support a hand and at least one retaining element adapted to retain the hand on said supporting portion during therapeutic treatment.

10. The device according to claim 1, further comprising vibration generation means operatively connected to said supporting elements to induce a vibration movement into said supporting elements.

* * * * *